(12) United States Patent
Biedermann et al.

(10) Patent No.: US 8,636,782 B2
(45) Date of Patent: Jan. 28, 2014

(54) RECEIVING PART FOR RECEIVING A ROD FOR COUPLING THE ROD TO A BONE ANCHORING ELEMENT AND BONE ANCHORING DEVICE WITH SUCH A RECEIVING PART

(75) Inventors: Lutz Biedermann, VS-Villingen (DE); Wilfried Matthis, Weisweil (DE); Berthold Dannecker, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 332 days.

(21) Appl. No.: 12/649,236

(22) Filed: Dec. 29, 2009

(65) Prior Publication Data

US 2010/0168801 A1 Jul. 1, 2010

Related U.S. Application Data

(60) Provisional application No. 61/141,191, filed on Dec. 29, 2008.

(30) Foreign Application Priority Data

Dec. 29, 2008 (EP) ..................................... 08022510

(51) Int. Cl.
*A61B 17/86* (2006.01)
*A61B 17/88* (2006.01)

(52) U.S. Cl.
USPC ........... 606/306; 606/305; 606/307; 606/308; 606/328; 606/279

(58) Field of Classification Search
USPC .................. 606/305–308, 319, 328, 266, 279
See application file for complete search history.

(56) References Cited

U.S. PATENT DOCUMENTS

| 5,549,608 A | 8/1996 | Errico et al. |
| 5,578,033 A | 11/1996 | Errico et al. |
| 5,584,834 A | 12/1996 | Errico et al. |

(Continued)

FOREIGN PATENT DOCUMENTS

| EP | 2 022 423 A1 | 2/2009 |
| WO | WO 2006/116437 A2 | 11/2006 |
| WO | WO 2007/038350 A2 | 4/2007 |
| WO | WO 2007/038351 A3 | 4/2007 |

OTHER PUBLICATIONS

European Search Report for European Application 08022510.5 in the name of Biedermann Motech GmbH, European Search Report dated Apr. 16, 2009 and mailed Apr. 27, 2009 (7 pgs.).

*Primary Examiner* — Eduardo C Robert
*Assistant Examiner* — Julianna N Harvey
(74) *Attorney, Agent, or Firm* — Christie, Parker & Hale, LLP

(57) ABSTRACT

A receiving part for receiving a rod for coupling the rod to a bone anchoring element includes a receiving part body including: a rod receiving portion with a channel for receiving a rod, and a head receiving portion for accommodating a head of a bone anchoring element, the head receiving portion having an open end and being flexible for inserting and clamping of the head, and an exterior surface with a curved portion; and a locking ring around the head receiving portion, wherein the locking ring has an interior surface with a curved portion for engagement with the curved portion of the exterior surface of the head receiving portion for locking a position of the head relative to the head receiving portion.

27 Claims, 7 Drawing Sheets

(56) References Cited

U.S. PATENT DOCUMENTS

| | | |
|---|---|---|
| 5,586,984 A | 12/1996 | Errico et al. |
| 5,609,593 A | 3/1997 | Errico et al. |
| 5,728,098 A * | 3/1998 | Sherman et al. ............. 606/269 |
| 5,733,285 A | 3/1998 | Errico et al. |
| 5,964,760 A | 10/1999 | Richelsoph |
| 6,010,503 A | 1/2000 | Richelsoph et al. |
| 6,254,602 B1 | 7/2001 | Justis |
| 6,355,040 B1 | 3/2002 | Richelsoph et al. |
| 6,582,436 B2 | 6/2003 | Schlapfer et al. |
| 7,090,674 B2 | 8/2006 | Doubler et al. |
| 7,585,315 B2 | 9/2009 | Donath |
| 2002/0032443 A1 | 3/2002 | Sherman et al. |
| 2003/0023240 A1 | 1/2003 | Amrein et al. |
| 2005/0080415 A1 * | 4/2005 | Keyer et al. .................. 606/61 |
| 2005/0096653 A1 | 5/2005 | Doubler et al. |
| 2005/0228385 A1 | 10/2005 | Iott et al. |
| 2005/0228392 A1 * | 10/2005 | Keyer et al. .................... 606/86 |
| 2006/0161153 A1 | 7/2006 | Hawkes et al. |
| 2006/0200128 A1 | 9/2006 | Mueller |
| 2007/0093817 A1 | 4/2007 | Barrus et al. |
| 2007/0288004 A1 | 12/2007 | Alvarez |
| 2008/0027432 A1 | 1/2008 | Strauss et al. |
| 2008/0243193 A1 | 10/2008 | Ensign et al. |
| 2009/0036934 A1 | 2/2009 | Biedermann et al. |
| 2009/0062867 A1 | 3/2009 | Schumacher |
| 2009/0105716 A1 | 4/2009 | Barrus |
| 2009/0105756 A1 | 4/2009 | Richelsoph |
| 2009/0105769 A1 | 4/2009 | Rock et al. |
| 2009/0105770 A1 | 4/2009 | Berrevoets et al. |
| 2009/0143827 A1 | 6/2009 | Levy et al. |
| 2009/0149887 A1 * | 6/2009 | Schlaepfer et al. ........... 606/278 |

* cited by examiner

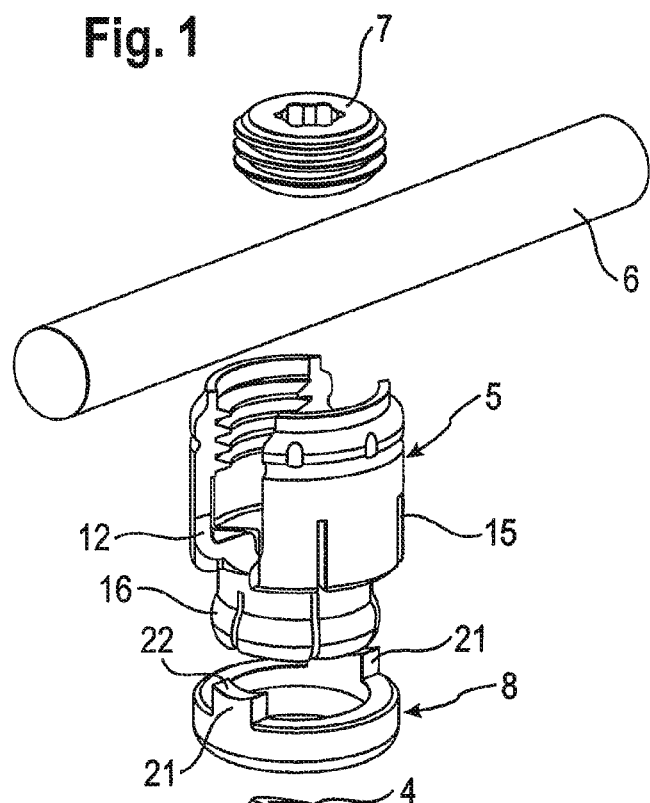
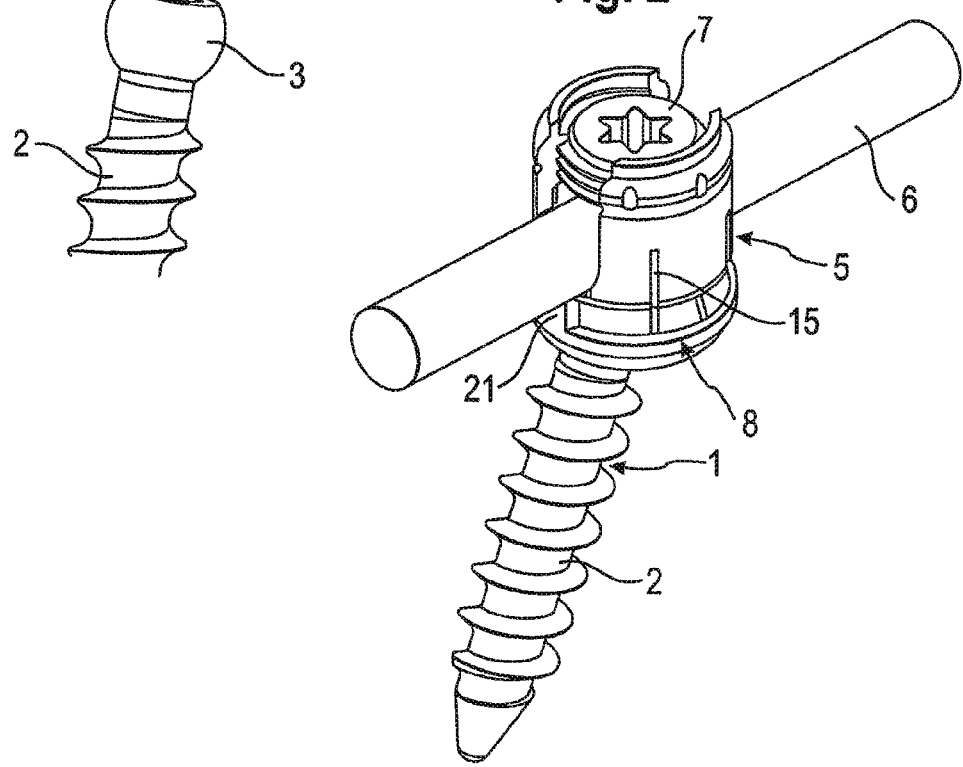

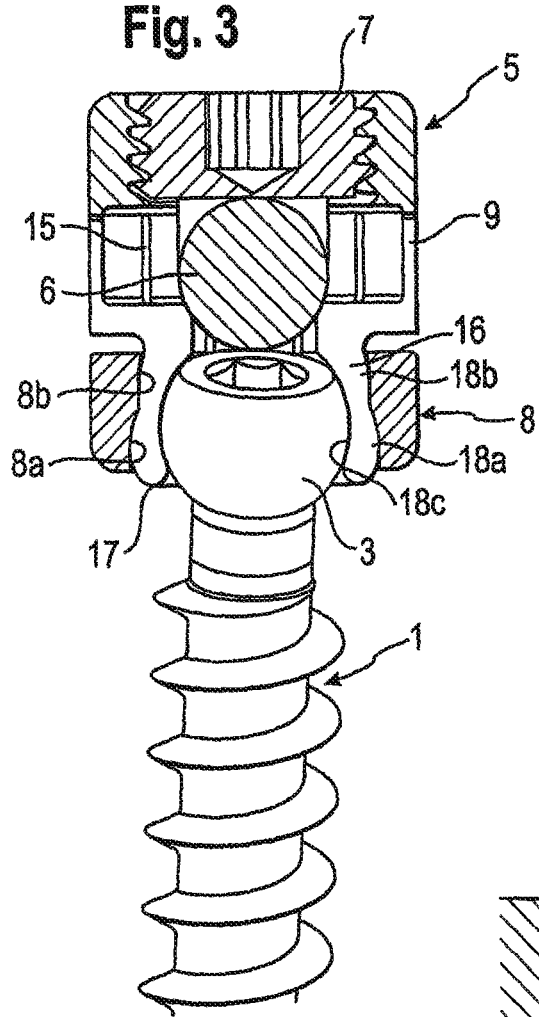
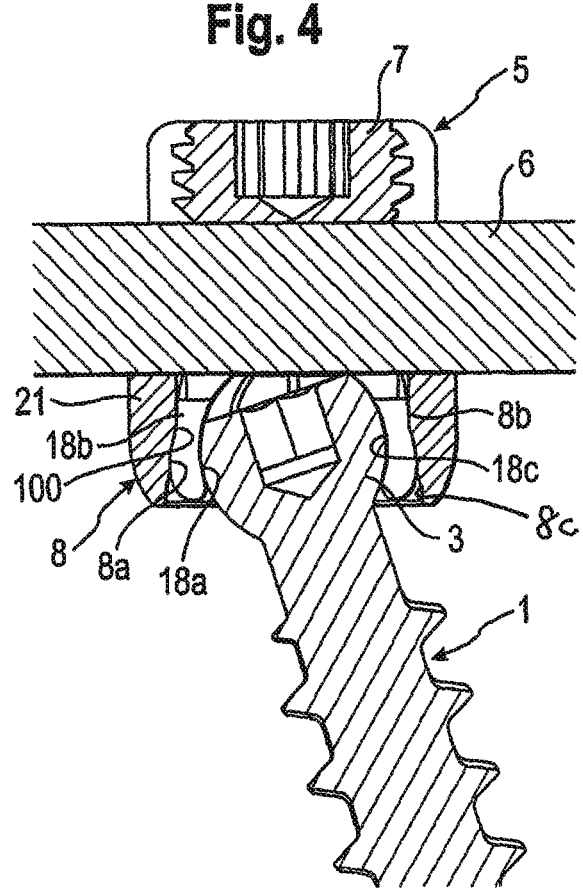

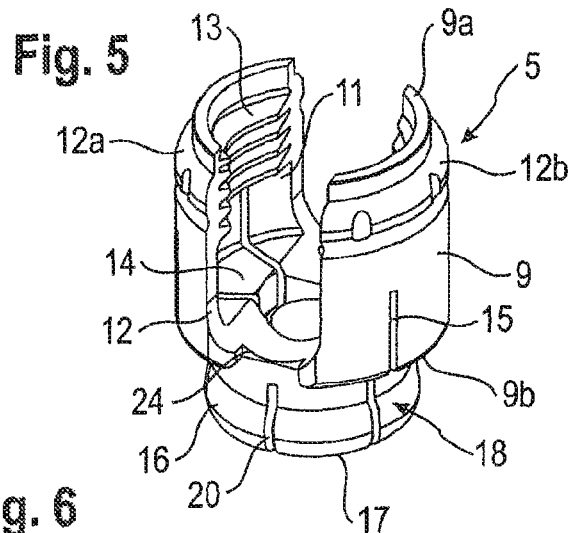
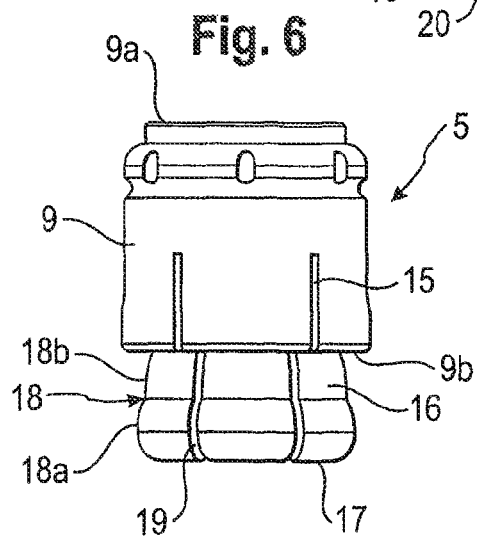
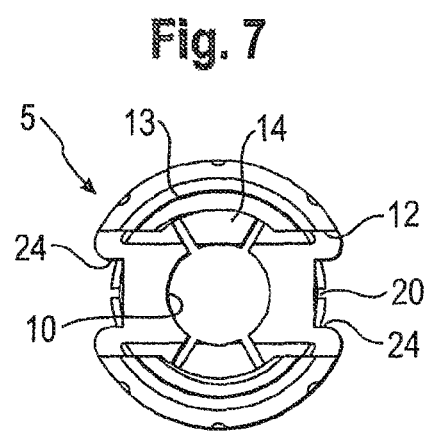
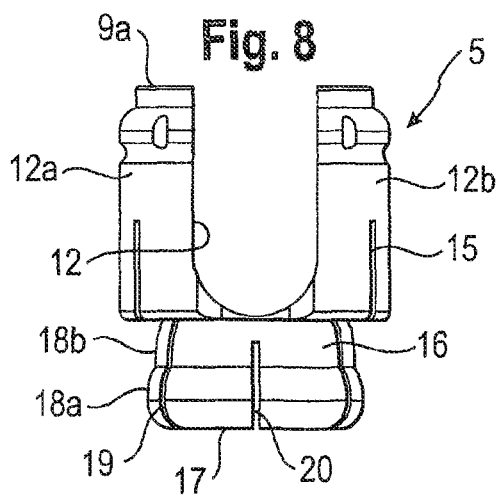
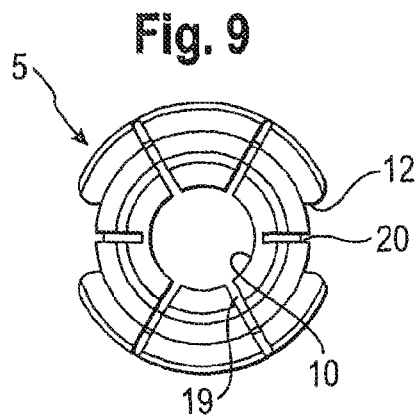

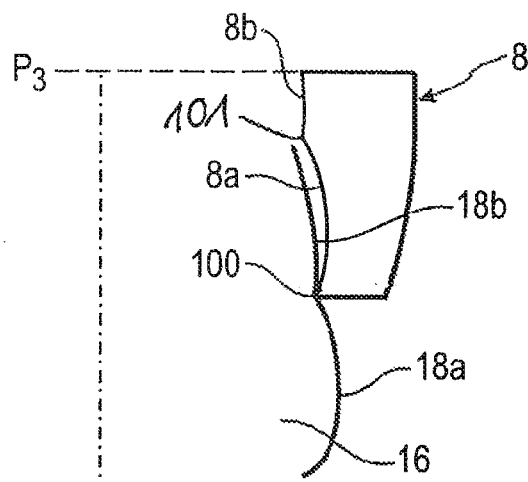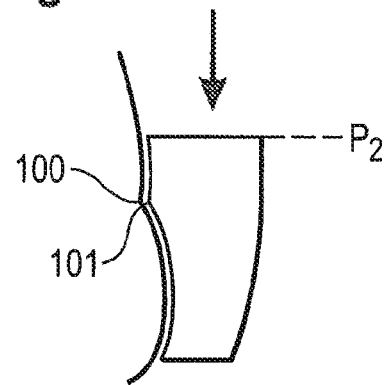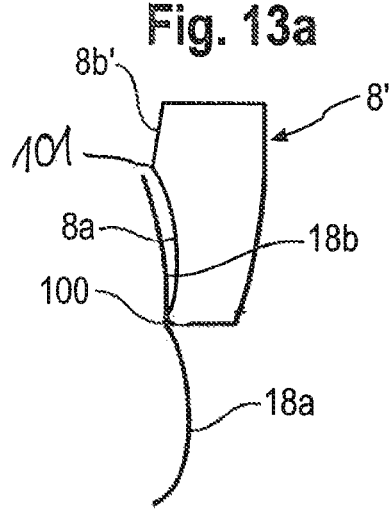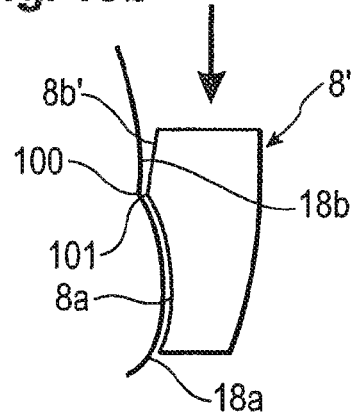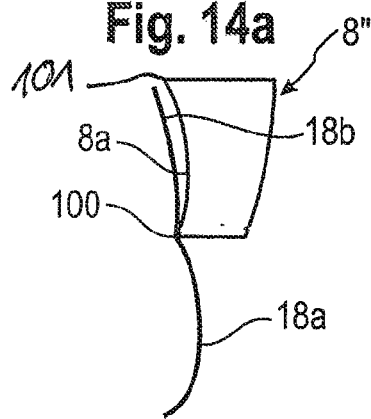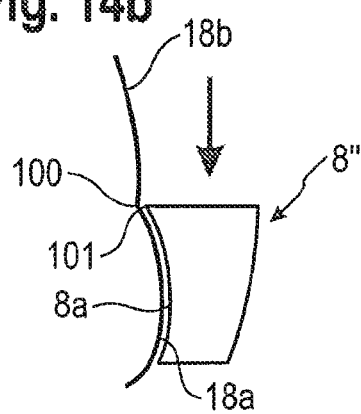

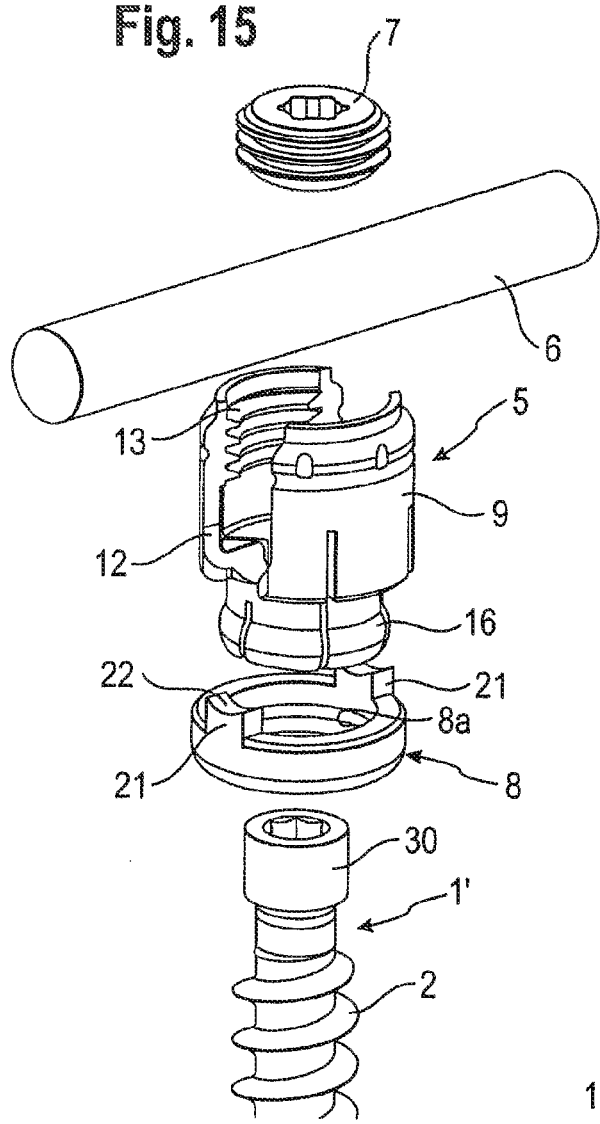
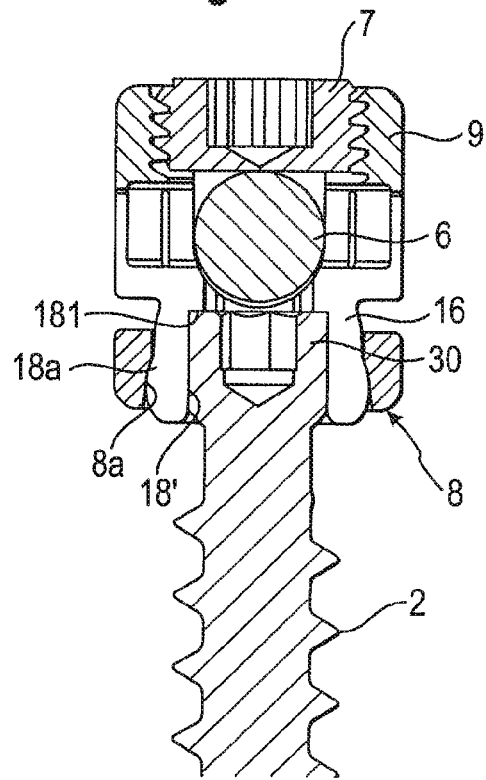

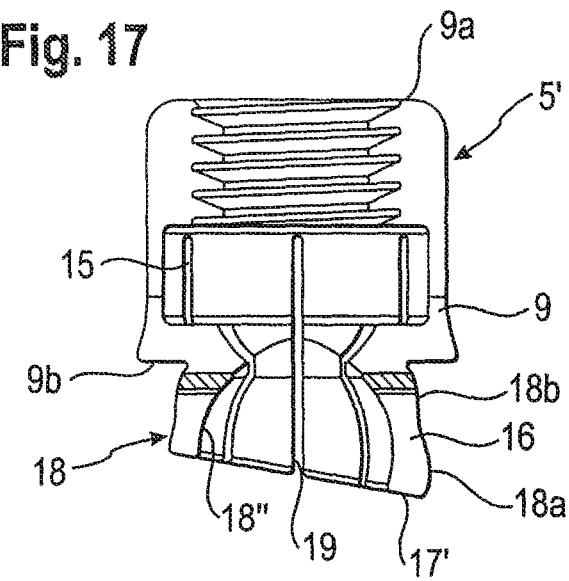
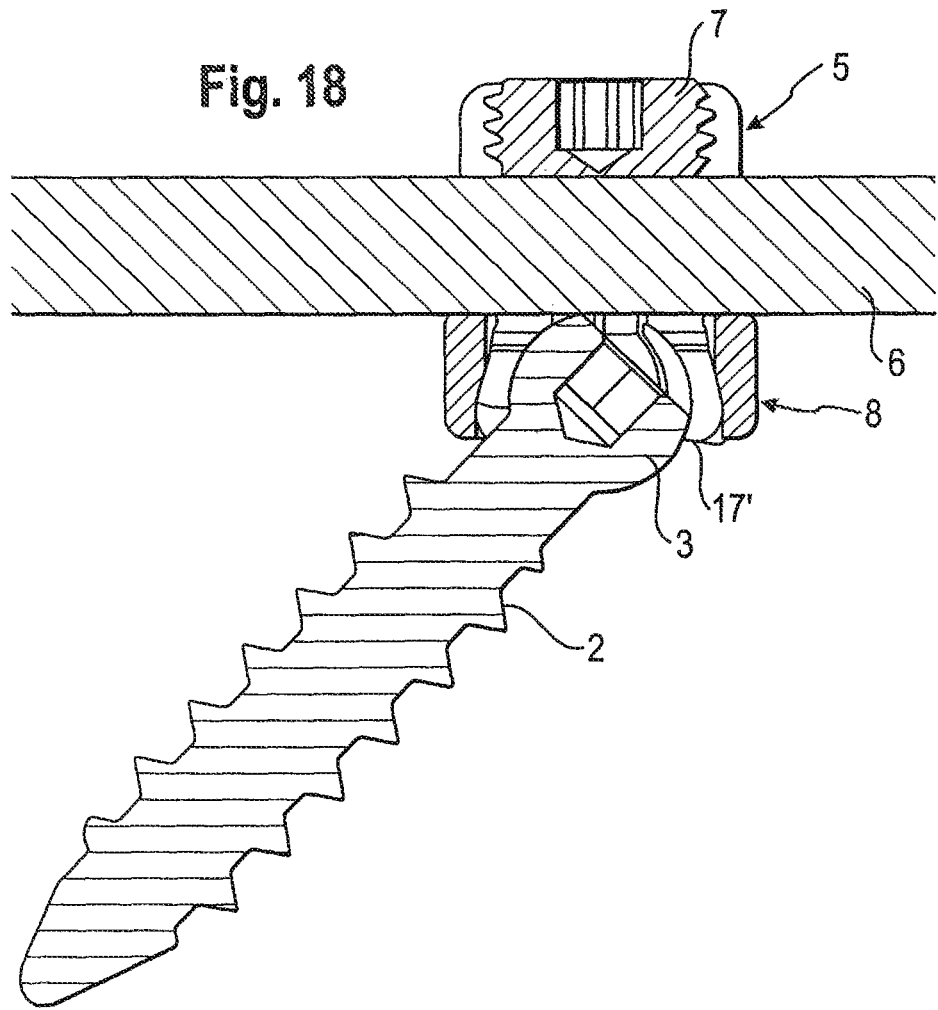

RECEIVING PART FOR RECEIVING A ROD FOR COUPLING THE ROD TO A BONE ANCHORING ELEMENT AND BONE ANCHORING DEVICE WITH SUCH A RECEIVING PART

CROSS-REFERENCE TO RELATED APPLICATIONS)

The present application claims the benefit of U.S. Provisional Patent Application Ser. No. 61/141,191, filed Dec. 29, 2008, the contents of which are hereby incorporated by reference in their entirety, and claims priority from European Patent Application EP 08 022 510.5, filed Dec. 29, 2008, the contents of which are hereby incorporated by reference in their entirety.

BACKGROUND

1. Field of the Invention

The invention relates to a receiving part for receiving a rod for coupling the rod to a bone anchoring element and a bone anchoring device with such a receiving part. The head of the bone anchoring element is locked in the receiving part by compression of a head receiving portion of the receiving part laterally surrounding the head by means of a locking ring. The head receiving portion of the receiving part has an exterior surface with a curved portion and the locking ring has an interior surface with a curved portion, which presses against the curved portion of the exterior surface of the head receiving portion to compress the head receiving portion so that the head is clamped. The bone anchoring device can be realized, for example, in the form of a polyaxial bone screw allowing a pivotal movement of the head.

2. Description of Related Art

U.S. Pat. No. 5,728,098 describes a bone screw for connection to a spinal rod comprising a screw element and a receiver member which has slits provided at the bottom of the rod receiving channel, and wherein two ring-shaped compression members made of a shaped-memory alloy are provided at the lower side and the upper side of the receiver member, respectively. The compression members contract about the portions of the receiver member when the temperature is elevated so that the rod is clamped in the channel.

U.S. Pat. No. 5,549,608 describes a polyaxial bone screw with a screw element with a spherical head and a coupling element to couple the screw element to a spinal rod. The coupling element has a tapered lower potion including a slotted interior chamber in which the spherical head is initially polyaxially disposed. The coupling element further comprises a recess for receiving the head. In addition, a locking ring surrounding the lower portion of the coupling element and a cylindrical rod securing sleeve, which fits over the coupling element, are provided. A top locking nut is used to exert pressure onto the rod securing sleeve. The head is locked in the interior chamber by means of the locking ring, which is pressed down by the rod securing sleeve.

U.S. Pat. No. 5,733,285 describes a similar polyaxial bone screw, wherein in one embodiment the rod securing sleeve is omitted and the rod directly presses onto a locking collar disposed around the tapered and colleted portion of the coupling element. The locking collar has to be placed onto the coupling element from above. It is not secured against escaping towards the upper end and against rotation when the rod is not inserted. Furthermore, the size of the known bone anchoring device is quite large, as the locking collar and the top locking nut extend substantially outward from the diameter of the coupling element.

WO 2007/038350 A2 discloses an apparatus for connecting a bone anchor to a support rod including a connector body and a cap. The connector body has a socket for insertion, angulation and removal of a bone anchor, the socket having a section with a spherical outer surface. A sleeve is provided, which is configured to fit over the connector body, the sleeve having a conical inside wall, which is tangential to the spherical outer surface of the spherical section. The circular contact zone provides uniform compression of the chamber receiving the bone anchor by the sleeve. The sleeve extends over the whole length of the socket.

US 2005/0080415 A1 describes a polyaxial bone anchor for attaching a rod to a bone comprising an anchor member and a body member having a U-shaped channel for receiving the rod and a compressible recess for receiving a head of the anchor member. A portion of an exterior surface of the compressible recess is tapered and a collar is slidably disposed about the body member. The collar comprises an interior surface portion which is tapered and which cooperates with the tapered exterior surface portion of the compressible recess.

SUMMARY

It is the object of the invention to provide an improved receiving part for receiving a rod for coupling the rod to a bone anchoring element and a bone anchoring device with such a receiving part, which has small size while simultaneously providing a safe final locking and/or which can be used as a modular system.

The bone anchoring device according to an embodiment of the invention comprises few elements, which reduces the costs of manufacturing and which facilitates handling. It makes use of the principle of clamping the head of the bone anchoring element circumferentially from the lateral sides, which reduces the force necessary to safely clamp the head. The design of the bone anchoring device allows to further reduce the dimension in terms of height as well as in terms of the bottom outer diameter, which is particularly suitable for applications, where small-sized anchoring devices are utilized, such as in the field of cervical spinal surgery or pediatric applications, trauma and minimally invasive applications.

The head of the bone anchoring element can be inserted into the receiving part at any time before or during surgery. Therefore, it is, for example possible to first anchor the bone anchoring element in the bone, and thereafter connect the bone anchoring element to the receiving part and the rod. By providing various bone anchors with different receiving parts, a modular system is available prior to surgery.

Since the height of the locking ring is smaller than the height of the head receiving portion, the receiving part has a profile with a small diameter. The pressure exerted via the locking ring onto the head receiving portion is largest at a position of the largest diameter of the head of the bone anchoring element. Therefore, the locking ring does not have to extend up to the open end of the head receiving portion, which allows for a locking ring with a reduced diameter at the bottom side.

A locking ring is movable between a position in which the head is not clamped and a position in which the head is locked. The locking ring can be releasably held in either of the two end positions, which makes handling very convenient. The locking ring may be held also in a preliminary locking position, which allows secondary adjustments of the rod while maintaining the angular position of the receiving part with respect to the bone anchoring element.

Since the locking ring has a curved interior surface portion, jamming between the locking ring and the head receiving portion does not occur.

BRIEF DESCRIPTION OF THE DRAWINGS

Further features and advantages of the invention will become apparent from the description of embodiments using the accompanying drawings. In the drawings:

FIG. 1 shows a perspective exploded view of a first embodiment of the bone anchoring device.

FIG. 2 shows a perspective view of the bone anchoring device of FIG. 1 in an assembled state.

FIG. 3 shows a sectional view of the bone anchoring device of FIG. 2 in the assembled state, the section being taken perpendicular to the rod axis.

FIG. 4 shows a sectional view of an embodiment of a bone anchoring device in an assembled state, the section being taken along the rod axis.

FIG. 5 shows a perspective view of the receiving part of the bone anchoring device of FIG. 1.

FIG. 6 shows a side view of the receiving part of FIG. 5.

FIG. 7 shows a top view of the receiving part of FIG. 5.

FIG. 8 shows another side view of the receiving part of FIG. 5 rotated by 90°.

FIG. 9 shows a bottom view of the receiving part of FIG. 5.

FIG. 12a shows a schematic view of a preliminary locking position of a locking ring.

FIG. 12b shows a locking position of the locking ring.

FIG. 13a shows a preliminary position of a modified locking ring.

FIG. 13b shows a locking position of the modified locking ring.

FIG. 14a shows a preliminary locking position of a further modified locking ring.

FIG. 14b shows a locking position of the further modified locking ring.

FIG. 15 shows an exploded perspective view of a second embodiment of the bone anchoring device.

FIG. 16 shows a sectional view of the second embodiment in an assembled state, the section being taken perpendicular to the rod axis.

FIG. 17 shows a sectional view of the receiving part according to a third embodiment.

FIG. 18 shows a sectional view of the bone anchoring device according to the third embodiment, the section being taken along the rod axis.

DETAILED DESCRIPTION

Figure 10:
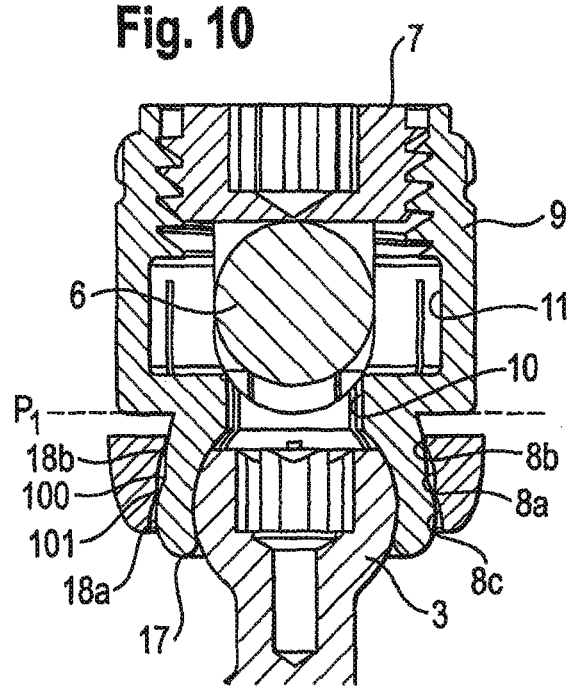
FIG. 10 shows a sectional view of an embodiment of a bone anchoring device similarly as illustrated in FIG. 4 in a position in which the bone anchoring element is still pivotable.

As shown in FIGS. 1 to 4, the bone anchoring device according to embodiments of the present invention comprise a bone anchoring element 1 in the form of a bone screw having a threaded shaft 2 and a head 3 with a curved surface portion, in these embodiments a spherical segment-shaped head. The head 3 has a recess 4 for engagement with a screwing-in tool. The bone anchoring device further comprises a receiving part body 5 for receiving a rod 6 to connect it to the bone anchoring element 1. Further, a closure element 7 in the form of an inner screw is provided for securing the rod 6 in the receiving part body 5. In addition, the bone anchoring device comprises a locking ring 8 for locking the head in the receiving part body 5.

As can be seen in particular in FIGS. 5 to 9, the receiving part body 5 comprises a rod receiving portion 9, which is substantially cylindrical and which has a first end 9a, and an opposite second end 9b. The rod receiving portion 9 has a coaxial first bore 10 provided at the second end 9b. The diameter of the first bore 10 is smaller than the diameter of the head 3 of the bone anchoring element. The rod receiving portion 9 also comprises a coaxial second bore 11 extending from the first end 9a to a distance from the second end 9b. The diameter of the second bore 11 is larger than that of the first bore 10 and larger than the diameter of the rod 6. A substantially U-shaped recess 12 is provided in the rod receiving portion 9, which extends from the first end 9a toward the second end 9b, the diameter of the recess 12 being slightly larger than the diameter of the rod 6 in such a way that the rod 6 can be placed in the recess 12 and can be guided therein. The recess 12 forms free legs 12a, 12b, on which an internal thread 13 is provided. The internal thread 13 can be a metric thread, a flat thread, a negative angle thread, a saw-tooth thread or any other thread type. Preferably, a thread form such as a flat thread or negative angle thread is used, which prevents splaying of the legs 12a, 12b, when the inner screw 7 is screwed in. The depth of the recess 12 is such that the rod 6 and the inner screw 7 can be inserted between the legs. Between the bottom of the recess 12 and the legs 12a, 12b a flat section 14 is provided, forming the end of the bore 11.

As can be seen in FIGS. 1, 5 and 7, cuts 24 are provided in the rod receiving portion on either end of the channel formed by the recess 12.

The rod receiving portion 9 of the receiving part body 5 further comprises a plurality of coaxial slits 15 extending from the second end 9b to a distance from the first end, wherein the distance corresponds approximately to the length of the internal thread 13. The slits 15 are open at the second end 9b and extend, as can be seen in particular in FIGS. 5, 7 and 9, through the flat section 14 and the substantially U-shaped recess 12. At least one slit 15, preferably more than one slit, is provided on either side of the recess 12. The number of slits is provided according to the degree of flexibility which is to be provided by the slits. It may depend, for example, on the material, the wall thickness, and/or other factors.

Adjacent to the second end 9b, the receiving part body 5 comprises a head receiving portion 16 providing an accommodation space for the head 3 of the bone anchoring element 1. The head receiving portion 16 has an open end 17 opposite to the second end 9b and an exterior surface 18. The open end 17 can have a rounded edge. As can be seen in particular in FIG. 6, the outer diameter of the rod receiving portion 9 at its second end 9b is larger than the outer diameter of the head receiving portion 16 adjacent to the second end 9b and is also larger than the outer diameter of the head receiving portion 16 at the open end 17. Hence, the head receiving portion 16 is recessed with respect to the rod receiving portion 9. The exterior surface 18 of the head receiving portion 16 has a first curved portion 18a and a second curved portion 18b with an outwardly directed curvature. The outer diameter of the second curved portion 18b is smaller than the outer diameter of the first curved portion 18a. In the embodiment shown, the curvature is substantially spherically-shaped. At the transition between the curved first surface portion 18a and the curved second surface portion 18b, a groove 100 is formed (see, e.g., FIG. 4).

As can be seen in particular in FIGS. 3 and 4, the head receiving portion 16 has an internal hollow section 18c forming a seat for the head 3 of the bone anchoring element 1. The hollow section 18c is adapted in its shape to the shape of the head 3, in the embodiment shown, it is a spherical section to accommodate the spherical head 3. The hollow section 18c is dimensioned in such a way that it encompasses the head 3 of the bone anchoring element from the side, covering a region including the largest diameter of the head 3.

As can be seen in particular in FIGS. 1, 2 and 5 to 9, a plurality of slits 19 are provided in the head receiving portion 16 which are open to the open end 17 and extend from the open end 17 to the second end 9b of the rod receiving portion, and which may continue into the slits 15 of the rod receiving portion 9, thereby forming continuous slits extending from the open end 17 of the head receiving portion into the rod receiving portion 9. The number of slits 19 may be equal to the number of slits 15, however, the number of slits can be smaller or larger depending on the desired flexibility of the head receiving portion 16. In addition, slits 20 are provided on the side of the head receiving portion 16 which is adjacent to the substantially U-shaped recess 12 of the rod receiving portion as shown in FIG. 6. The slits 20 end at a distance from the second end 9b. The flexibility of the head receiving portion 16 is such that the head 3 of the anchoring element 1 can be inserted by expanding the head receiving portion 16 and can be clamped by compressing the head receiving portion 16. The slits 15 in the rod receiving portion facilitate mounting of the receiving part body 5 onto the head 3 manually, for example, at any time before or during surgery.

The locking ring will now be described with reference to FIGS. 1 to 4. The locking ring 8 has a substantially cylindrical outer surface with an outer diameter corresponding substantially to the outer diameter of the rod receiving portion 9 of the receiving part body 5. The height of the locking ring 8 in an axial direction is smaller than that of the head receiving portion 16 of the receiving part body 5, so that, as shown in particular in FIG. 3, there is a distance or gap between the locking ring and a second end 9b of the receiving part 5. As shown in FIGS. 1 and 3 to 4, the locking ring 8 has on its inner side a first interior surface portion 8a which is curved. The curvature is directed outward from the center of the locking ring. In the embodiment shown, the curved first interior surface portion 8a has a spherical curvature which is sized to fit to the first curved exterior surface portion 18a of the head receiving portion 16. The radius of the curvature is preferably smaller than the radius of curvature of the head 3. The dimensions of the locking ring 8 with respect to its inner portions are such that the locking ring 8 can be moved along the outer surface of the head receiving portion 16, thereby compressing the head receiving portion 16 when moved downward.

Figure 11:
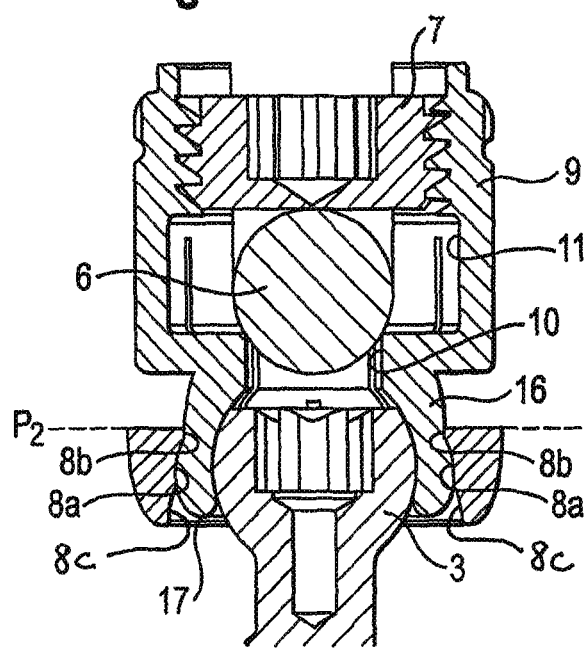
FIG. 11 shows a sectional view of the bone anchoring device of FIG. 10 in a position in which the head of the bone anchoring element is locked.

Adjacent to the curved first interior surface portion 8a, in some embodiments, the locking ring 8 may have a curved second interior surface portion 8b with a curvature corresponding to that of the second curved exterior surface portion 18b of the head receiving portion 16. At the transition between the first interior surface portion 8a and the second interior surface portion 8b, a circular edge 101 is formed as shown in FIGS. 10 and 12. En addition, on a side of the curved first interior surface portion 8a opposite to the curved second interior surface portion 8b, the locking ring 8 may have a third portion 8c with a diameter increasing towards the free end of the locking ring 8, for example, as illustrated in the embodiments of FIGS. 4, 10, and 11.

As can be seen in particular in FIGS. 1 and 4, the locking ring 8 further comprises on its side facing the second end 9b, two projections 21 located diametrically opposite to each other. The projections 21 have a height such that they project above the bottom of the substantially U-shaped recess 12 and extend into the cuts 24, when the locking ring 8 is in a position in which the head 3 is not yet clamped. The free end 22 of the projections 21 can be curved, particularly inwardly curved, with a curvature corresponding to that of the rod 6. The locking ring 8 is arranged in such a way around the head receiving portion 16 of the receiving part body 5 that the projections are located at the positions of the recess 12. By means of this, the projections 21 which project into the recess 12, prevent the locking ring from rotating when the rod is not inserted.

The flexibility of the head receiving portion 16 and the size of the head receiving portion 16 at the open end 17 allows mounting of the locking ring 8 by assembling it from the free end 17 onto the head receiving portion 16. Since the outer diameter of the head receiving portion 16 is smaller than that of the rod receiving portion 9, the locking ring 8 does not project or only minimally projects beyond the rod receiving portion in a radial direction.

The inner screw 7 has a thread corresponding to the internal thread 13 provided on the legs 12a, 12b. If a thread which prevents the legs from splaying is used, a single closure element such as the inner screw 7 is sufficient. This reduces the size of the bone anchoring device in a radial direction.

The receiving part body 5, the locking ring 8, the inner screw 7 and the bone anchoring element 1 are made of a bio compatible material, for example, of titanium or stainless steel or a bio-compatible alloy or bio compatible plastic material with sufficient strength.

The bone anchoring device may be pre-assembled with a locking ring 8 mounted on the head receiving portion 16 of the receiving part body 5 from the open end 17. Alternatively, the bone anchoring element 1 can be pre-assembled with the receiving part 5 and the locking ring 8.

The locking of the head 3 is now explained with respect to FIGS. 10 to 12. When the rod is not yet inserted or not pressed into the recess 12, the locking ring is movable between a first position $P_1$, in which it abuts against the second end 9b of the rod receiving part which acts as a stop (not shown), and a second position $P_2$ near the open end 17 of the head receiving portion as shown in the embodiments of FIGS. 11 and 12b, which is defined by the locking of the head 3 by means of compression of the head receiving portion. An example of a transition position between the first position $P_1$ and the second position $P_2$ is illustrated in FIG. 10. In the position $P_2$ as shown in the embodiments of FIG. 11 and FIG. 12b, the curved interior surface portion 8a of the locking ring 8 presses onto the first curved exterior surface portion 18a of the head receiving portion 16 to clamp the head 3 by means of compression of the head receiving portion 16. The dimensions of the locking ring 8 and the head receiving portion 16 are such that the matching curved first surface portions 8a, 18a of the locking ring 8 and the head receiving portion 16 are located at the position of the greatest outer diameter of the head 3. As shown in the embodiments of FIG. 11 and FIG. 12b in the locking position $P_2$, the second curved portion 8b of the locking ring and 18b of the head receiving portion also oppose each other. The edge 101 engages the groove 100 so that a form fit force contribution for the locking of the head is provided. This forms an obstacle, when the locking ring is moved in the direction of the first position $P_1$ which enhances the safe and secure clamping of the head 3 in the locking position $P_2$.

Means for temporarily and releasably holding the locking ring in the first position $P_1$ may be provided (not shown). This can be in the form of a catch, for example.

Depending on the dimensions of the curvatures and the radii of the curved portions, there may be a third intermediate position $P_3$ as shown in FIG. 12a in which the lower end of the curved surface portion 8a of the locking ring 8 engages the groove 100 between the two curved exterior surface portions of the head receiving portion 16. In this way, the locking ring 8 is in a loosely held position, in which it also may exert a slight compression force onto the head receiving portion 16 to allow a preliminary locking of the head 3. The preliminary locking of the head 3 may allow for rotation of the head 3 in the head receiving portion 16 with application of additional force, but may prevent removal of the head from the head receiving portion.

The bone anchoring device can be used in several ways. In one way of use, the bone anchoring element 1, the receiving part body 5 and the locking ring 8 are pre-assembled. The bone anchoring element is screwed into the bone with the receiving part mounted to the anchoring element. The recess 4 of the head 3 can be accessed with the screwing-in tool through the first bore 10. The locking ring 8 is in its first position close to the second end 9b, where it does not clamp the head 3. The flexible receiving part creates a slight pretension having a small overlap on the inner curved surface of the hollow portion 18c. In this state the head 3 is pivotably held in the second portion 16, which allows the receiving part body 5 to be safely aligned to receive the rod 6. Once the correct position of the rod with respect to other bone anchoring devices is achieved, the inner screw 7 is screwed in between the legs 12a, 12b until it presses onto the rod 6. The rod is pressed against the bottom of the substantially U-shaped recess, thereby engaging the free ends 22 of the projections 21, respectively, and shifting the locking ring 8 down. When the locking ring 8 is moved down, it reaches the intermediate position $P_3$, in which a preliminary locking of the head 3 is possible. When it moves further down towards the free end 17 of the head receiving portion 16, it compresses the head receiving portion 16, thereby clamping the head 3. The force clamping the head 3 is generated by the frictional force between the locking ring 8 and the head receiving portion 16.

As shown in FIGS. 11 and 12b, the end position $P_2$ is secured in addition by a form-fit contribution generated by the engagement of the edge 101 with the groove 100. Since the force which is exerted by the locking ring 8 acts by utilizing the interior curved surface 8a from the lateral side, the force necessary for safely immobilizing the head is smaller than in the case in which the force acts from above on the top of the head 3. It also allows the device to be reduced in size by allowing the wall thickness of the receiving part to be reduced. Final tightening of the inner screw 7 locks the rod 6 and the head 3 simultaneously.

In another way of use, only the receiving part body 5 and the locking ring 8 are pre-assembled. The bone anchoring element 3 is first screwed into the bone and then the receiving part is mounted onto the head 3, while the locking ring 8 is in its first position close to the second end 9b and does not compress the second portion 16. Alternatively, the bone anchoring element 1 and the receiving part body 5 with the pre-assembled locking ring 8 are assembled by pressing the receiving part onto the head 3. This allows to select the appropriate bone anchoring element in terms of diameter, length and other features of the anchoring section. Hence, a modular system can be provided including receiving parts and several bone anchoring elements, which then individually can be chosen and adapted.

In yet another way of use, the inner screw 7 is tightened to lock the head 3 and the rod 6. Thereafter, the inner screw 7 is loosened to allow further adjustments of the rod 6. The head 3 remains temporarily clamped due to the frictional force and the shape of the curvatures, which holds the locking ring 8 in place.

In FIGS. 13a and 13b the interaction between a modified locking ring 8' and the head receiving portion is schematically shown. The modified locking ring 8' has instead of the second curved interior surface portion 8b a conically widening interior portion 8b'. At the transition between the curved portion 8a and the conically widening portion 8b' an edge 101 is built in the same way as in the previous embodiment, which engages in the groove 100 formed at the transition between the curved first surface portion 18a and the curved second surface portion 18b of the head receiving portion 16.

In FIGS. 14a and 14b a further modification of the locking ring, which cooperates with the head receiving portion is schematically shown. The locking ring 8'' has only an interior curved portion 8a, which forms an edge 101, which engages in the groove 100 formed between the first curved exterior surface portion 18a and the second curved exterior surface portion 18b of the head receiving portion 16.

FIGS. 15 and 16 show a second embodiment of the bone anchoring device. Portions and elements which are similar to the first embodiment and its modifications are designated with the same reference numerals as in the description of the first embodiment. The descriptions thereof will not be repeated.

The second embodiment differs from the first embodiment only with respect to the bone anchoring element and the hollow space in the head receiving portion 16 of the receiving part body 5. The bone anchoring element 1' has a threaded shaft 2 and a cylindrical head 30. The hollow portion 18' is cylindrically-shaped and has a diameter, which is slightly larger than the diameter of the cylindrical head 30 in such a way that the cylindrical head 30 can be inserted and guided in the hollow portion 18' in the unlocked state. The end 181 of the cylindrical hollow portion forms a stop for the head 30. The use of the bone anchoring device according to the second embodiment is similar to that of the first embodiment. The difference is that the receiving part 5 can not pivot relative to the bone anchoring element 1 but can only rotate in the unclamped state of the head 30. This monoaxial rotatable connection between the receiving part body 5 and the bone anchoring element 1' may be useful in certain anatomical situations. It allows the receiving part to be aligned with respect to the rod by only rotating it around the screw axis.

FIGS. 17 and 18 show a third embodiment of the bone anchoring device. Portions and elements which are similar to the first and second embodiments are designated with the same reference numerals, and the detailed descriptions thereof will not be repeated. The receiving part body 5' of the third embodiment comprises an inclined free end 17' of the head receiving portion 16. As can be seen in particular in FIG. 17, the inclined free end 17' defines a plane, which forms an angle with the plane defined by the first end 9a of the rod receiving portion of the receiving part body 5. The hollow portion 18'', which accommodates the head 3, is therefore shorter on one side compared to the opposite side.

As can be seen in FIG. 18, this results in a larger pivot angle to one side as compared to the opposite side. Hence, a polyaxial screw with an asymmetric pivot angle range is provided. The inclined free end 17' can be easily manufactured, for example, by cutting.

Further modifications of the embodiments described are possible. For example, the head of the bone anchoring element can have any other shape, such as, for example, a conical shape. The internal hollow portion 18 of the head receiving portion can be adapted to the shape of the head. In a further modification, the receiving part body 5 or at least the head receiving portion 16 are made of a bio-compatible plastic material which provides elasticity to a certain degree. In this case, the slits may be omitted.

The projections of the locking ring which engage the rod can also have any other shape. For example, the surface of the free end can be flat or otherwise shaped. In a further modification, the projections are omitted.

The curvature of the cooperating surfaces of the head receiving portion and the locking ring can be other than spherical. The radii of the curvature can be the same or can be different.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part for receiving a rod for coupling the rod to a bone anchoring element, the receiving part comprising:
a receiving part body comprising:
a rod receiving portion with a channel for receiving a rod, and
a head receiving portion for accommodating a head of a bone anchoring element, wherein a longitudinal axis extends from the rod receiving portion to the head receiving portion, the head receiving portion having an open end and being flexible for inserting and clamping of the head, and an exterior surface with a curved portion having a convexly curved profile along a direction of the longitudinal axis; and
a locking ring configured to be arranged around the head receiving portion,
wherein the locking ring has an interior surface with a curved portion, such that when the locking ring is around the head receiving portion, the curved portion of the locking ring has a curved profile with a first section increasing in diameter and a second section decreasing in diameter along a direction parallel to the longitudinal axis for engagement with the curved portion of the exterior surface of the head receiving portion for locking a position of the head relative to the head receiving portion.

2. The receiving part of claim 1, wherein the curved portion of the locking ring has a concave curvature.

3. The receiving part of claim 1, wherein the curved portion of the head receiving portion is a first curved portion, and the head receiving portion further comprises a second curved portion adjacent to the first curved portion and a groove between the first and second curved portions.

4. The receiving part of claim 3, wherein the first and second curved portions of the head receiving portion have a convex curvature, and the curved portion of the locking ring has a concave curvature.

5. The receiving part of claim 3, wherein an end of the curved portion of the locking ring forms an edge configured to cooperate with the groove of the head receiving portion.

6. The receiving part of claim 1, wherein the locking ring is movable between a first position in which the head receiving portion is not compressed for providing movement of the head and a second position in which the head is clamped in the head receiving portion to lock the position of the head relative to the head receiving portion.

7. The receiving part of claim 6, wherein the locking ring engages the head receiving portion in the second position in a form locking manner.

8. The receiving part of claim 6, wherein the locking ring is closer to the open end of the head receiving portion in the second position than in the first position.

9. The receiving part of claim 6, further comprising a third position between the first position and the second position in which the head is preliminarily locked in the head receiving portion.

10. The receiving part of claim 1, further comprising a bone anchoring element, wherein a head of the bone anchoring element has a curved outer surface portion, and wherein a radius of curvature of the curved portion of the locking ring is smaller than a radius of curvature of the curved outer surface portion of the head.

11. The receiving part of claim 1, wherein the locking ring is configured to move upon exerting a pressure onto the locking ring via the rod.

12. The receiving part of claim 1, wherein the rod receiving portion comprises a first end and a second end, and a recess extends from the first end in the direction of the second end to form the channel.

13. The receiving part of claim 1, wherein the rod receiving portion has a first end and a second end, and the head receiving portion is arranged at the side of the second end, and wherein an outer diameter of the head receiving portion adjacent to the second end is smaller than an outer diameter of the rod receiving portion at the second end.

14. The receiving part of claim 1, wherein the head receiving portion comprises a plurality of slits adjacent to the open end.

15. The receiving part of claim 1, wherein the rod receiving portion has a first end and a second end, the head receiving portion being at the second end, wherein the rod receiving portion has a plurality of slits extending from the second end to a distance from the first end.

16. The receiving part of claim 15, wherein at least one of the plurality of slits extends continuously from the open end of the head receiving portion to a distance from the first end of the rod receiving portion.

17. The receiving part of claim 1, wherein the curved portion of the locking ring is a first curved portion, and the locking ring further comprises a second curved portion adjacent to the first curved portion, and an edge between the first and second curved portions.

18. The receiving part of claim 1, wherein the locking ring further comprises a conically widening interior portion adjacent to the curved portion of the locking ring and an edge between the conically widening interior portion and the curved portion of the locking ring.

19. The receiving part of claim 1, wherein for at least a portion of the locking ring, the curved portion is bounded by two edges defining first and second ends along a longitudinal axis of the locking ring, respectively.

20. The receiving part of claim 1, wherein the rod receiving portion of the receiving part body has an end on a side opposite the head receiving portion defining a plane, and the open end of the head receiving portion is inclined relative to the defined plane.

21. A bone anchoring device comprising:
a bone anchoring element having a threaded shaft and a head; and
a receiving part for receiving a rod for coupling the rod to the bone anchoring element, the receiving part comprising:
a receiving part body comprising a rod receiving portion with a channel for receiving the rod, and a head receiving portion for accommodating the head of the bone anchoring element, wherein a longitudinal axis extends from the rod receiving portion to the head receiving portion, the head receiving portion having an open end and being flexible for inserting and clamping of the head, and an exterior surface with a curved portion having a convexly curved profile along a direction of the longitudinal axis; and a locking ring configured to be arranged around the head receiving portion, wherein the locking ring has an interior surface with a curved portion, such that when the locking ring is around the head receiving portion, the curved portion of the locking ring has a curved profile with a first section increasing in diameter and a second section decreasing in diameter along a direction parallel to the longitudinal axis for engagement with the curved portion of the exterior surface of the head receiving portion for locking a position of the head relative to the head receiving portion.

22. The bone anchoring device according to claim 21, wherein a closure element is provided for securing the rod in the channel.

23. A method of coupling a rod to a bone anchoring element via a receiving part, the receiving part comprising a rod receiving portion with a channel for receiving the rod, a head receiving portion, wherein a longitudinal axis extends from the rod receiving portion to the head receiving portion, the head receiving portion having an open end and being flexible for inserting and clamping of a head of the bone anchoring element and an exterior surface with a curved portion having a convexly curved profile along a direction of the longitudinal axis, and a locking ring around the head receiving portion and having an interior surface with a curved portion having a curved profile with a first section increasing in diameter and a second section decreasing in diameter along a direction parallel to the longitudinal axis for engagement with the curved portion of the exterior surface of the head receiving portion, the method comprising:

introducing the head of the bone anchoring element into the open end of the head receiving portion;

pivoting the head receiving portion relative to the head to align the receiving part with the rod;

inserting the rod into the channel of the rod receiving portion;

advancing a closure element in the channel to push the rod against the locking ring; and further advancing the closure element in the channel towards the head receiving portion to force the locking ring towards the open end of the head receiving portion via the rod and to lock a position of the rod relative to the receiving part, wherein advancement of the locking ring towards the open end of the head receiving portion engages the curved portion of the locking ring with the curved portion of the exterior surface of the head receiving portion to compress the head receiving portion and lock the position of the bone anchoring element relative to the receiving part.

24. The method of claim 23, further comprising inserting the bone anchoring element into a bone prior to the introduction of the head of the bone anchoring element into the open end of the head receiving portion.

25. The method of claim 23, further comprising inserting the bone anchoring element into a bone after the introduction of the head of the bone anchoring element into the open end of the head receiving portion.

26. The method of claim 23, wherein prior to the engagement of the curved portion of the locking ring and the curved portion of the exterior surface of the head receiving portion, the locking ring is advanced to a preliminary locking position where the position of the bone anchoring element relative to the receiving part is loosely held.

27. A receiving part for receiving a rod for coupling the rod to a bone anchoring element, the receiving part comprising:

a receiving part body comprising:

a rod receiving portion with a channel for receiving a rod, and a head receiving portion for accommodating a head of a bone anchoring element, wherein a longitudinal axis extends from the rod receiving portion to the head receiving portion, the head receiving portion having an open end and being flexible for inserting and clamping of the head, and an exterior surface with a first curved portion, a second curved portion adjacent to the first curved portion, and a groove or an edge separating the first and second curved portions, wherein the first and second curved portions each has a curved profile along a direction of the longitudinal axis; and a locking ring configured to be arranged around the head receiving portion, wherein the locking ring has an interior surface with a curved portion, such that when the locking ring is around the head receiving portion, the curved portion of the locking ring has a curved profile with a first section increasing in diameter and a second section decreasing in diameter along a direction parallel to the longitudinal axis for engagement with at least one of the first or second curved portions of the exterior surface of the head receiving portion for locking a position of the head relative to the head receiving portion.

\* \* \* \* \*

UNITED STATES PATENT AND TRADEMARK OFFICE
CERTIFICATE OF CORRECTION

| | | |
|---|---|---|
| PATENT NO. | : 8,636,782 B2 | Page 1 of 1 |
| APPLICATION NO. | : 12/649236 | |
| DATED | : January 28, 2014 | |
| INVENTOR(S) | : Biedermann et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 471 days.

Signed and Sealed this
Twenty-first Day of April, 2015

Michelle K. Lee
*Director of the United States Patent and Trademark Office*